(12) United States Patent
Shen et al.

(10) Patent No.: US 10,558,035 B2
(45) Date of Patent: Feb. 11, 2020

(54) OBSERVATION MASK OF DERMATOSCOPE

(71) Applicant: Zumax Medical Co., Ltd, Suzhou, Jiangsu (CN)

(72) Inventors: Shunguo Shen, Jiangsu (CN); Jianyue Li, Jiangsu (CN); Xiaohua Yang, Jiangsu (CN); Xiaotian Chen, Jiangsu (CN)

(73) Assignee: ZUMAX MEDICAL CO., LTD (CN)

( * ) Notice: Subject to any disclaimer, the term of this patent is extended or adjusted under 35 U.S.C. 154(b) by 0 days.

(21) Appl. No.: 15/316,486

(22) PCT Filed: Dec. 29, 2014

(86) PCT No.: PCT/CN2014/095426
§ 371 (c)(1),
(2) Date: Dec. 5, 2016

(87) PCT Pub. No.: WO2015/184781
PCT Pub. Date: Dec. 10, 2015

(65) Prior Publication Data
US 2017/0184842 A1    Jun. 29, 2017

(30) Foreign Application Priority Data

Jun. 5, 2014  (CN) .......................... 2014 1 0246760

(51) Int. Cl.
*G02B 27/00* (2006.01)
*A61B 5/00* (2006.01)
*G02B 1/04* (2006.01)

(52) U.S. Cl.
CPC ........ *G02B 27/0006* (2013.01); *A61B 5/0077* (2013.01); *A61B 5/44* (2013.01);
(Continued)

(58) Field of Classification Search
CPC ...... G02B 27/0006; G02B 23/16; G02B 1/04; A61B 5/44
(Continued)

(56) References Cited

U.S. PATENT DOCUMENTS 5,093,940 A * 3/1992 Nishiyama ................ A61F 9/02
2/440
6,898,030 B1 * 5/2005 Lin ........................ G02B 7/006
359/740
(Continued)

FOREIGN PATENT DOCUMENTS

CN    103181154 A    6/2013
CN    202960442 U    6/2013
(Continued)

Primary Examiner — Jade R Chwasz
(74) Attorney, Agent, or Firm — Schmeiser, Olsen & Watts, LLP

(57) ABSTRACT

Disclosed is an observation mask of a dermatoscope (3), comprising a mask body (1) connected to the front end of the dermatoscope (3), and an observation lens (2) arranged on the mask body (1), wherein the mask body (1) and the observation lens (2) are of the same non-metallic material, the observation lens (2) and the mask body (1) are provided integrally, and the observation lens (2) is transparent. The observation mask has a simple structure, is easy to install, can be used in a disposable way, is safe and healthy, and also protects a lens surface of the dermatoscope (3).

16 Claims, 2 Drawing Sheets

(52) U.S. Cl.
CPC ................ *A61B 5/441* (2013.01); *G02B 1/04* (2013.01); *A61B 2562/247* (2013.01)

(58) Field of Classification Search
USPC .................................................. 359/507, 511
See application file for complete search history.

(56) References Cited

U.S. PATENT DOCUMENTS

| | | | |
|---|---|---|---|
| 8,011,504 B1* | 9/2011 | Farberov | A61B 1/00135 206/316.1 |
| 2004/0062056 A1 | 4/2004 | Helmut et al. | |
| 2004/0095502 A1* | 5/2004 | Losehand | H01L 24/97 348/340 |
| 2004/0174525 A1 | 9/2004 | Mullani | |
| 2011/0164312 A1 | 7/2011 | Adamo | |
| 2014/0243685 A1* | 8/2014 | Patwardhan | A61B 5/44 600/476 |

FOREIGN PATENT DOCUMENTS

| | | |
|---|---|---|
| CN | 203138453 U | 8/2013 |
| WO | WO2012056641 A2 | 5/2012 |

\* cited by examiner

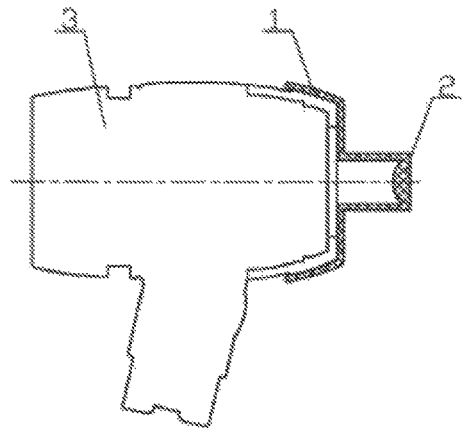
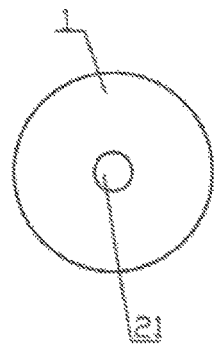
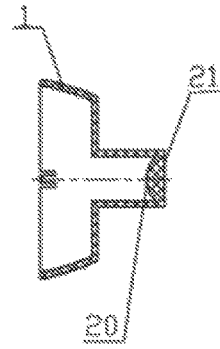
FIGURE 5　　　　　　FIGURE 6a　　　　FIGURE 6b
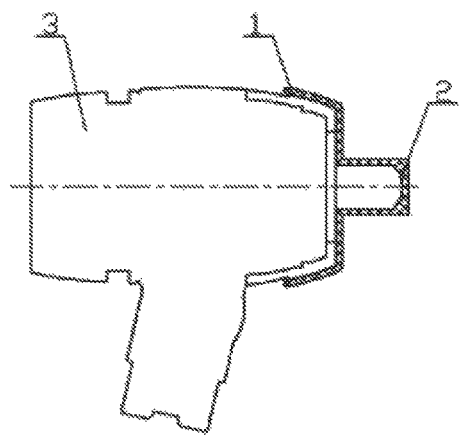
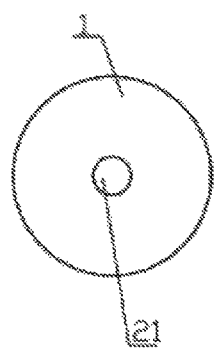
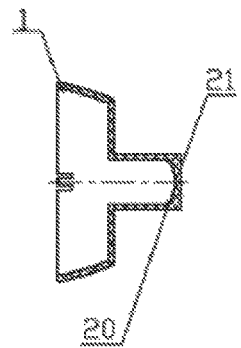
FIGURE 7　　　　　　FIGURE 8a　　　　FIGURE 8b

OBSERVATION MASK OF DERMATOSCOPE

RELATED APPLICATIONS

This application claims priority from International Patent Application No. PCT/CN2014/095426, filed Dec. 29, 2014, which claims priority to CN201410246760.0 filed Jun. 5, 2014, the entire disclosures of which are incorporated herein by this reference.

FIELD OF INVENTION

The present invention relates to an observation mask of a dermatoscope.

BACKGROUND OF THE INVENTION

The skin is the largest organ of human body, and a dermatoscope is usually utilized to conduct external optical imaging of this organ, check the health condition of skin tissue, and diagnose neoplastic lesions. The dermatoscope is expensive, and usually requires to be used repeatedly, and each time when used, the front-end detection working surface thereof fits human skin adhered with dusts and bacteria, and it is easy to cause cross-infection after repeated use. Therefore, the detection working surface of the dermatoscope must be disinfected after each use, which is fussy to operate, and is a waste of time; it is likely to wear the lens surface after many times.

SUMMARY OF THE INVENTION

The present invention is intended to provide an observation mask of a dermatoscope.

To achieve the above purpose, the technical schemes employed by the present invention are:

an observation mask of a dermatoscope, comprises a mask body connected to the front end of the dermatoscope, and an observation lens arranged on the mask body, wherein the mask body and the observation lens are of the same non-metallic material, the observation lens and the mask body are provided integrally, and the observation lens is transparent.

Preferably, the material of the observation mask is PMMA.

Preferably, the observation lens has an internal surface and an external surface, the external surface of the observation lens being a detection working surface, and the internal surface and the external surface are plane or spherical or non-spherical.

Preferably, the mask body is nontransparent or frosted.

Preferably, the mask body is connected with the front end of the dermatoscope via a buckle, an elastic slot or a screw thread.

Preferably, the observation mask is formed in one via a mould.

Preferably, the observation mask is formed in one by plastic injection molding or stretching molding.

Due to the use of the above technical schemes, the present invention has the following advantages and effects over the prior art:

The observation mask has a simple structure, is easy to install, can be used in a disposable way, is safe and healthy, and also protects the lens surface of the dermatoscope.

BRIEF DESCRIPTION OF THE DRAWINGS

FIG. 5 is a diagram of Embodiment 3 in the using state;
FIG. 6 is a schematic diagram of Embodiment 3;
FIG. 7 is a diagram of Embodiment 4 in the using state;
FIG. 8 is a schematic diagram of Embodiment 4.

Wherein, 1—mask body; 2—observation lens; 20—internal surface; 21—external surface; 3—dermatoscope.

DETAILED DESCRIPTION OF EXEMPLARY EMBODIMENTS

In the following, the present invention are explained in detail combining the embodiments with the accompanying drawings:

Embodiment 1

Figure 2A:
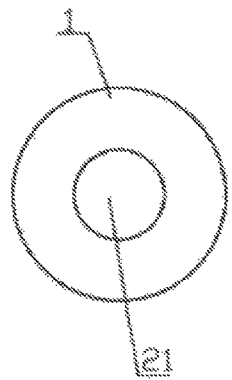
FIG. 2 is a schematic diagram of Embodiment 1.
Figure 2B:
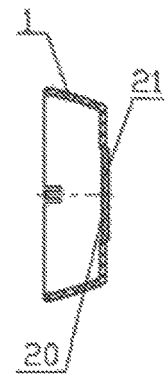

An observation mask of a dermatoscope as shown in FIG. 2, comprises a mask body 1 and an observation lens 2 on the front of the mask body 1, the mask body 1 and the observation lens 2 are of the same non-metallic material such as PMMA (polymethyl methacrylate), and provided integrally, for example, by plastic injection molding or stretching molding.

The observation lens 2 is a sheet-shaped lens, and this observation lens 2 with the sheet-shaped lens has an internal surface 20 and an external surface 21, the external surface 21 of the observation lens 2 being a detection working surface, and the internal surface 20 being plane.

The mask body 1 is nontransparent or frosted, and the rear part of the mask body 1 is connected with the front part of the dermatoscope 3 via a buckle, an elastic slot or a screw thread, for example, a buckle is provided on the rear part of the mask body, a buckle slot is provided on the front part of the dermatoscope 3, and the connection is achieved by matching up the buckle and the buckle slot; or, screw threads are provided in the rear part of the mask body 1 and the front part of the dermatoscope 3, respectively, and the two are threaded connected.

Figure 1:
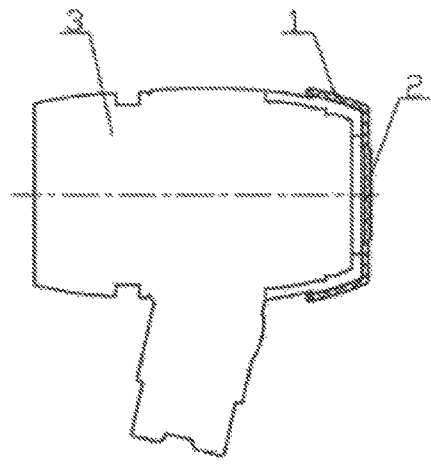
FIG. 1 is a diagram of Embodiment 1 in the using state.

As shown in FIG. 1, when in use, the mask body 1 is sleeved in front of the dermatoscope 3, and the external surface 21 of the observation lens 2 is fitted to skin, and diagnosis for a large area of skin may be implemented since the area of the external surface 21 of the sheet-shaped lens is large.

Embodiment 2

Figure 4A:
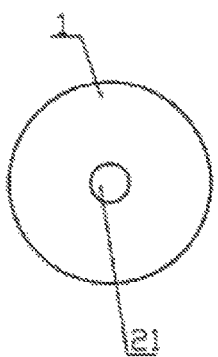
FIG. 4 is a schematic diagram of Embodiment 2.
Figure 4B:
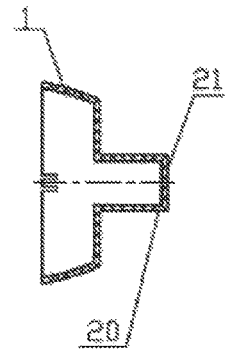

An observation mask of a dermatoscope as shown in FIG. 4, comprises a mask body 1 and an observation lens 2 on the front of the mask body 1, the mask body 1 and the observation lens 2 are of the same non-metallic material such as PMMA (polymethyl methacrylate), and provided integrally, for example, by plastic injection molding or stretching molding.

The observation lens 2 is a T-shaped lens, and this observation lens 2 with the T-shaped lens has an internal surface 20 and an external surface 21, the external surface 21 of the observation lens 2 being a detection working surface, and the internal surface 20 being plane.

The mask body 1 is nontransparent or frosted, and the rear part of the mask body 1 is connected with the front part of the dermatoscope 3 via a buckle, an elastic slot or a screw thread, for example, a buckle is provided on the rear part of the mask body, a buckle slot is provided on the front part of the dermatoscope 3, and the connection is achieved by matching up the buckle and the buckle slot; or, screw threads are provided in the rear part of the mask body 1 and the front part of the dermatoscope 3, respectively, and the two are threaded connected.

Figure 3:
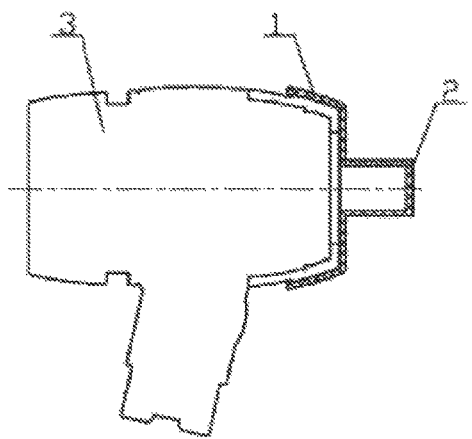
FIG. 3 is a diagram of Embodiment 2 in the using state.

As shown in FIG. 3, when in use, the mask body 1 is sleeved in front of the dermatoscope 3, and the external surface 21 of the observation lens 2 is fitted to skin, and diagnosis for a small area of skin may be implemented since the area of the external surface 21 of the T-shaped lens is small and can extend into a groove.

Embodiment 3

An observation mask of a dermatoscope as shown in FIG. 6, comprises a mask body 1 and an observation lens 2 on the front of the mask body 1, the mask body 1 and the observation lens 2 are of the same non-metallic material such as PMMA (polymethyl methacrylate), and provided integrally, for example, by plastic injection molding or stretching molding.

The observation lens 2 is a T-shaped lens, and this observation lens 2 with the T-shaped lens has an internal surface 20 and an external surface 21, the external surface 21 of the observation lens 2 being a detection working surface, and the internal surface 20 being convex spherical to increase the magnifying power.

The mask body 1 is nontransparent or frosted, and the rear part of the mask body 1 is connected with the front part of the dermatoscope 3 via a buckle, an elastic slot or a screw thread, for example, a buckle is provided on the rear part of the mask body, a buckle slot is provided on the front part of the dermatoscope 3, and the connection is achieved by matching up the buckle and the buckle slot; or, screw threads are provided in the rear part of the mask body 1 and the front part of the dermatoscope 3, respectively, and the two are threaded connected.

As shown in FIG. 5, when in use, the mask body 1 is sleeved in front of the dermatoscope 3, and the external surface 21 of the observation lens 2 is fitted to skin, and diagnosis for a small area of skin may be implemented since the area of the external surface 21 of the T-shaped lens is small and can extend into a groove.

Embodiment 4

An observation mask of a dermatoscope as shown in FIG. 8, comprises a mask body 1 and an observation lens 2 on the front of the mask body 1, the mask body 1 and the observation lens 2 are of the same non-metallic material such as PMMA (polymethyl methacrylate), and provided integrally, for example, by plastic injection molding or stretching molding.

The observation lens 2 is a T-shaped lens, and this observation lens 2 with the T-shaped lens has an internal surface 20 and an external surface 21, the external surface 21 of the observation lens 2 being a detection working surface, and the internal surface 20 being concave spherical to increase the working distance.

The mask body 1 is nontransparent or frosted, and the rear part of the mask body 1 is connected with the front part of the dermatoscope 3 via a buckle, an elastic slot or a screw thread, for example, a buckle is provided on the rear part of the mask body, a buckle slot is provided on the front part of the dermatoscope 3, and the connection is achieved by matching up the buckle and the buckle slot; or, screw threads are provided in the rear part of the mask body 1 and the front part of the dermatoscope 3, respectively, and the two are threaded connected.

As shown in FIG. 7, when in use, the mask body 1 is sleeved in front of the dermatoscope 3, and the external surface 21 of the observation lens 2 is fitted to skin, and diagnosis for a small area of skin may be implemented since the area of the external surface 21 of the T-shaped lens is small and can extend into a groove.

The embodiments described above are only for illustrating the technical concepts and features of the present invention, and intended to make those skilled in the art being able to understand the present invention and thereby implement it, and should not be concluded to limit the protective scope of this invention. Any equivalent variations or modifications according to the spirit of the present invention should be covered by the protective scope of the present invention.

What is claimed is:

1. An observation mask for a dermatoscope utilized to conduct external optical imaging of human body's skin, check a health condition of skin tissue, and diagnose neoplastic lesions, the observation mask comprising:
    a mask body having an interior surface and an exterior surface, wherein the mask body has a circular cross-section; and
    an observation lens that is non-separable and integrally formed with the mask body, the observation lens and the mask body being made from a same non-metallic material;
    wherein the mask body is removably attachable to a front end of the dermatoscope, such that when the mask body is attached to the dermatoscope, the interior surface of the mask body directly contacts the dermatoscope;
    wherein the mask body is frosted and the observation lens is transparent.

2. The observation mask according to claim 1, wherein the non metallic material of the observation mask is polymethyl methacrylate.

3. The observation mask according to claim 1, wherein the observation lens has an internal surface and an external surface, the external surface of the observation lens being a working surface for detection, and the internal surface and the external surface are plane or spherical or non-spherical.

4. The observation mask according to claim 1, wherein the mask body is connected with the front end of the dermatoscope via a buckle, an elastic slot or a screw thread.

5. The observation mask according to claim 1, wherein the observation mask is formed in one via a mold.

6. The observation mask according to claim 5, wherein the observation mask is formed in one by plastic injection molding or stretch molding.

7. The observation mask according to claim 1, wherein the observation lens is T-shaped.

8. The observation mask according to claim 1, wherein the mask body is symmetrical along each plane of symmetry which extends transverse to the observation lens.

9. A dermatoscope kit utilized to conduct external optical imaging of human body's skin, check a health condition of skin tissue, and diagnose neoplastic lesions, the dermatoscope kit comprising:
    a dermatoscope body with a transilluminating light source, standard magnifying optics, and a front end detection working surface;
    a first detachable polymethyl methacrylate protective cover positioned over the front end detection working surface, the first detachable polymethyl methacrylate protective cover comprising a transparent observation lens such that the observation lens becomes a detection working surface, wherein the first detachable polymethyl methacrylate protective cover is removable from the dermatoscope body and replaceable with additional detachable polymethyl methacrylate covers positioned on the front end detection working surface;

wherein the first detachable polymethyl methacrylate protective cover has a concave shape such that an interior surface of the first detachable polymethyl methacrylate protective cover directly contacts the dermatoscope body and the first detachable polymethyl methacrylate protective cover extends past a front face of the front end detection working surface of the dermatoscope body along an outer surface of the dermatoscope body;

wherein the first detachable polymethyl methacrylate protective cover has a shaped observation lens and the additional detachable polymethyl methacrylate protective covers each have a shaped observation lens that is different than the shaped observation lens of the first detachable polymethyl methacrylate protective cover.

10. An observation mask for a dermatoscope including a transilluminating light source, standard magnifying optics, and a front end detection working surface configured to conduct external optical imaging of human body's skin, check a health condition of skin tissue, and diagnose neoplastic lesions, the observation mask comprising:

a mask body having an interior surface and an exterior surface, wherein the interior surface of the mask body contacts a front end of the dermatoscope, and a portion of the mask body extends past the front end of the dermatoscope along an outer surface of the body of the dermatoscope; and an observation lens that is non-separable and integrally formed with the mask body, wherein the mask body and the observation lens are of the same non-metallic material, and at least the observation lens portion of the mask is transparent.

11. The observation mask according to claim 10, wherein the non metallic material of the observation mask is polymethyl methacrylate.

12. The observation mask according to 10, wherein the observation lens has an internal surface and an external surface, the external surface of the observation lens being a working surface for detection, and the internal surface and the external surface are plane or spherical or non-spherical.

13. The observation mask according to claim 10, wherein the mask body is frosted.

14. The observation mask according to claim 10, wherein the mask body is connected with the front end of the dermatoscope via a buckle, an elastic slot or a screw thread.

15. The observation mask according to claim 10, wherein the observation mask is formed in one via a mold.

16. The observation mask according to claim 15, wherein the observation mask is formed in one by plastic injection molding or stretch molding.

\* \* \* \* \*